United States Patent [19]

Käsbauer et al.

[11] Patent Number: 5,101,075
[45] Date of Patent: Mar. 31, 1992

[54] PROCESS FOR THE PREPARATION OF BIS-AND TRIS-(3-DIMETHYLAMINOPROPYL)-AMINE

[75] Inventors: Josef Käsbauer, Wermelskirchen; Helmut Fiege, Leverkusen; Wolfgang Kiel, Odenthal, all of Fed. Rep. of Germany

[73] Assignee: Bayer Aktiengesellschaft, Leverkusen, Fed. Rep. of Germany

[21] Appl. No.: 594,266

[22] Filed: Oct. 2, 1990

[30] Foreign Application Priority Data

Oct. 26, 1989 [DE] Fed. Rep. of Germany ....... 3935641

[51] Int. Cl.$^5$ ............................................. C07C 209/48
[52] U.S. Cl. .................................................... 564/490
[58] Field of Search ......................................... 564/490

[56] References Cited

U.S. PATENT DOCUMENTS 3,821,305  6/1974  Bartalini et al. ................ 260/583 K
4,101,466  7/1978  McEntire ............................. 521/115

FOREIGN PATENT DOCUMENTS 2839134  3/1980  Fed. Rep. of Germany .

Primary Examiner—GLennon H. Hollrah
Assistant Examiner—Shailendra Kumar
Attorney, Agent, or Firm—Sprung Horn Kramer & Woods

[57] ABSTRACT

Bis- and tris-(3-dimethylaminopropyl)-amine can be prepared by catalytic hydrogenation of 3-(dimethylamino)-propionitrile with a palladium catalyst on an $Al_2O_3$-containing support.

9 Claims, No Drawings

PROCESS FOR THE PREPARATION OF BIS-AND TRIS-(3-DIMETHYLAMINOPROPYL)AMINE

BACKGROUND OF THE INVENTION

The present invention relates to a process for the preparation of bis- and tris-(3-dimethylaminopropyl)-amine by catalytic hydrogenation of 3-(dimethylamino)-propionitrile. In this connection, palladium catalysts are employed on an $Al_2O_3$-containing support.

Bis- and tris-(3-dimethylaminopropyl)-amines are important auxiliaries for the preparation of polyurethane foams (DE-OS German Published Specification) 3,048,832, DE-OS (German Published Specification) 2,624,528, U.S. Pat. No. 4,255,528, U.S. Pat. No. 4,431,753). The preparation of bis-(3-dimethylaminopropyl)-amine is described, for example, in U.S. Pat. No. 4,101,466, U.S. Pat. No. 4,143,071 and DE-OS (German Published Specification) 3,048,832. However, only low product yields are obtained in all cases or the selectivity is only satisfactory with a low conversion. The purification of the product is consequently complicated and unsuitable for an industrial process.

The preparation of tris-(3-dimethylaminopropyl)-amine is described, for example, in DE-PS (German Patent Specification) 2,624,528. N,N-bis-(3-dimethylaminopropyl)-propylene-1,3-diamine is methylated here with formaldehyde in the presence of formic acid according to Leuckart-Wallach. However, this method of preparation starts from an expensive intermediate and requires corrosive and aggressive chemicals.

According to J. Chem. Soc. (A) 1971, 2024, the tertiary amine mentioned in the above paragraph is prepared by reaction of tris-(3-hydroxypropyl)-amine with thionyl chloride and subsequently with an excess of dimethylamine. The duration of the reaction of 24 hours is very long. For working-up, excess 40% strength potassium hydroxide solution is added to the reaction solution and it is extracted with ether. This method of preparation is impracticable from the industrial and ecological point of view. Yields are also not mentioned.

Thus, there is therefore no reaction path described for the preparation of the substances mentioned in the title which starts from simple and economical compounds and yields the tertiary amine in good yields. A need for such a process thus existed.

SUMMARY OF THE INVENTION

A process for the prepration of bis-(3-dimethylaminopropyl)-amine and tris-(3-dimethylaminopropyl)-amine by catalytic hydrogenation of 3-(dimethylamino)-propionitrile has been found, which is characterized in that a palladium catalyst is employed on an $Al_2O_3$-containing support.

DETAILED DESCRIPTION OF THE INVENTION $Al_2O_3$-containing supports which may be mentioned are, for example, $\gamma$-$Al_2O_3$ or spinel. The palladium content of such a catalyst is 0.1-10% by weight, preferably 0.5-5% by weight, relative to the total weight of the catalyst.

The temperature of the process according to the invention is 50°-150° C. The pressure in the process according to the invention is 50-300 bar.

In the process according to the invention, a mixture of the bis-amine mentioned and the tris-amine mentioned is obtained which can be separated in a known manner, for example by distillation.

The advantages of the process according to the invention are in the high yield of the compounds mentioned, in carrying it out as a one-step process (one-pot process), in the easily accessible catalyst which can be prepared in a manner which is basically known to the person skilled in the art, for example by impregnation of the support with palladium compounds, in the long stability of the catalyst with unchanged activity and in the simple working-up of the reaction mixture.

The product yields increase with elevated pressure and with simultaneously or independently thereof reduced temperature.

In the context of the process according to the invention, some interesting variants have furthermore been found which allow, with fluctuating demand for the bis-amine or the tris-amine, the one desired in each case to be obtained in higher yield. Thus, it has been found that with the use of $Al_2O_3$ as the catalyst support the secondary bis-amine is preferably formed, while a spinel as the support material leads in an increased amount to the tertiary tris-amine.

If $Al_2O_3$ is employed as the catalyst support to increase the selectivity for the bis-amine, one with a large surface area, for example 200–500 $m^2/g$, preferably 300–450 $m^2/g$, is advantageous, since with smaller internal surface areas the activity of such a catalyst rapidly decreases.

When using a spinel as the support for the palladium catalyst, the tris-amine mentioned is obtained as the principal product. Possible spinel-forming elements are, for example, Li, Be, Mg, Zn, Mn, Cu and Ni. In preference, LiAl spinel may be mentioned as the support material.

In a further important variant of the process according to the invention, the starting mixture for the process according to the invention can be used to influence the product composition. For this purpose, 3-dimethylamino-propylamine, which is formed by sole hydrogenation of the nitrile group of 3-(dimethylamino)-propionitrile, is used. Thus, a mixture of 3-(dimethylamino)-propionitrile and 3-dimethylamino-propylamine in the approximately stoichiometric range leads to increased formation of the secondary bis-amine, while an excess of nitrile or the sole use of nitrile yields the tertiary tris-amine as the principal product.

Of course, the variants mentioned (different support materials and/or co-use of 3-dimethylamino-propylamine or leaving it out) can be combined with one another, increases in the desired direction being obtained.

In the case of the co-use of 3-dimethylamino-propylamine, this is employed in an amount of 20–80 mol-%, preferably 40–60 mol-%, relative to the mixture of 3-dimethylamino-propylamine and 3-(dimethylamino)-propionitrile.

EXAMPLE 1

0.5 mol of 3-(dimethylamino)-propionitrile and 0.5 mol of 3-(dimethylamino)-propylamine were hydrogenated at 80°–90° C. and 100 bar in a 0.3 l VA autoclave with the addition of 3 g of a catalyst consisting of 3.7% Pd on $\gamma$-$Al_2O_3$ (surface area 400 $m^2$). After a hydrogenation time of 2 hours, 93 g of a product mixture were obtained which was composed of 81.5% of bis-(3-dimethylaminopropyl)-amine and 3.8% of tris-(3-dimethylaminpropyl)-amine. The two products could easily

EXAMPLE 2

1 mol of 3-(dimethylamino)-propionitrile was hydrogenated at 120° C. and 100 bar in a 0.7 l VA autoclave with the addition of 3 g of the catalyst from Example 1. After a hydrogenation time of 2.5 hours, 88 g of product mixture were obtained which was composed of 32% of secondary and 48% of tertiary amine.

EXAMPLE 3

10 mol of 3-(dimethylamino)-propionitrile and 30 g of catalyst consisting of 4% Pd of LiAl spinel were hydrogenated at 120° C. and 220 bar in a 3 l VA autoclave. After a hydrogenation time of 1.5 hours, 860 g of product mixture were isolated which contained 31% of secondary and 58% of tertiary amine.

EXAMPLE 4 (Comparison example)

0.1 mol of 3-(dimethylamino)-propionitrile and 0.9 mol of 3-dimethylaminopropylamine were hydrogenated as in Example 1. After a hydrogenation time of 2 hours, 95.5 g of a product mixture were obtained which was composed only of 21.5% of secondary and 0.1% of tertiary amine.

What is claimed is:

1. A process for the preparation of bis-(3-dimethylaminopropyl)-amine and tris-(3-dimethylaminopropyl)-amine, wherein 3-(dimethylamino)-propionitrile is catalytically hydrogenated with a palladium catalyst on an $Al_2O_3$-containing support.

2. The process of claim 1, wherein $\gamma$-$Al_2O_3$ is employed as the $Al_2O_3$-containing support.

3. The process of claim 1, wherein the palladium content is 0.1–10% by weight relative to the total weight of the catalyst.

4. The process of claim 3, wherein the palladium content is 0.5–5% by weight, relative to the total weight of the catalyst.

5. The process of claim 1, wherein $Al_2O_3$ is employed as the support to increase the selectivity for bis-(3-dimethylaminopropyl)-amine.

6. The process of claim 5, wherein an $Al_2O_3$ having a surface area of 200–500 $m^2$/g is employed.

7. The process of claim 6, wherein an $Al_2O_3$ having a surface area of 300–450 $m^2$/g is employed.

8. The process of claim 1, wherein the 3-(dimethylamino)-propionitrile is employed in a mixture with 3-dimethylaminopropylamine for greater formation of bis-(3-dimethylaminopropyl)-amine, 3-dimethylaminopropylamine making up 20–80 mol-% of this mixture.

9. The process of claim 8, wherein 40–60 mol-% of 3-dimethylamino-propylamine is employed.

* * * * *